United States Patent
Nakanishi et al.

(10) Patent No.: US 6,717,003 B2
(45) Date of Patent: Apr. 6, 2004

(54) SILICONE COMPOUND, A POWDER SURFACE-TREATED WITH THIS COMPOUND, AND A MAKEUP CONTAINING THIS POWDER

(75) Inventors: Tetsuo Nakanishi, Gunma-ken (JP); Ichiro Ono, Gunma-ken (JP); Toru Shimizu, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 391 days.

(21) Appl. No.: 09/773,671

(22) Filed: Feb. 2, 2001

(65) Prior Publication Data

US 2001/0018044 A1 Aug. 30, 2001

(30) Foreign Application Priority Data

Feb. 4, 2000 (JP) .................................. 2000-027790

(51) Int. Cl.$^7$ .................................. C07F 7/04
(52) U.S. Cl. .................. 556/437; 556/446; 424/401; 424/65; 424/63; 424/60; 424/70.12; 523/209; 523/213; 523/216; 514/772.3
(58) Field of Search ................ 556/437, 446; 424/401, 65, 63, 60, 78.03, 70.12; 523/209, 213, 216; 514/772.3

(56) References Cited

U.S. PATENT DOCUMENTS

| | | |
|---|---|---|
| 3,502,769 A | 3/1970 | Nobukazu |
| 4,336,246 A | 6/1982 | Leon-Pekarek |
| 4,801,445 A | 1/1989 | Fukui et al. |
| 5,505,937 A | 4/1996 | Castrogiovanni et al. |
| 5,911,974 A | 6/1999 | Brieva et al. |

FOREIGN PATENT DOCUMENTS

GB  2124081 A  2/1984

*Primary Examiner*—Samuel Barts
(74) *Attorney, Agent, or Firm*—Millen, White, Zelano & Branigan, P.C.

(57) ABSTRACT

This invention relates to a powder which is surface-treated by a novel silicone compound, and to a makeup containing this powder. In particular, it relates to a silicone compound which has good compatibility with oils such as ester oils and triglycerides or silicone oils, and to a makeup with a smooth feel, excellent dispersibility and excellent emulsification stability.

A silicone compound represented by the general formula (1):

$$R^1_a R^2_b R^3_c SiO_{(4-a-b-c)/2}$$

(in the formula, $R^1$ is at least one organic group chosen from alkyl having 1–30 carbon atoms, aryl, aralkyl, fluorine-substituted alkyl or organopolysiloxanylsilyl, $R^2$ is a reactive substituent group chosen from hydrogen, hydroxy or alkoxy having 1–6 carbon atoms, or a reactive substituent group in which at least one of carbon, oxygen and silicon are bonded to these reactive substituent groups, $R^3$ is a carboxylate residue represented by the following general formula (2):

$$R^4CO_2-Q-$$

$R^4$ is a saturated or unsaturated hydrocarbon group having 2–30 carbon atoms, Q is a bivalent hydrocarbon group which may also contain a hetero atom, a is 1.0–2.5. b is 0.001–1.5, and c is 0.001–1.5, a powder surface-treated with this silicone compound, and a makeup containing this powder.

27 Claims, No Drawings

SILICONE COMPOUND, A POWDER SURFACE-TREATED WITH THIS COMPOUND, AND A MAKEUP CONTAINING THIS POWDER

A novel silicone compound, a powder surface-treated with this compound, and a makeup containing this powder.

FIELD OF THE INVENTION

This invention relates to a powder which is surface-treated by a novel silicone compound, and to a makeup containing this powder. In particular, it relates to a silicone compound which has good compatibility with oils such as ester oils and triglycerides or silicone oils, and to a makeup with a smooth feel, excellent dispersibility and excellent emulsification stability.

BACKGROUND OF THE INVENTION

In general, male secretions such as sweat, tears and sebum, lead to messy makeup, and sebum secreted from the skin becomes mixed with the oil in which the makeup is blended. This is a major reason why too much wetting of the powder in the makeup leads to messy makeup. To reduce the oil in makeup remaining on the skin, it has been attempted to use volatile oils, such as octamethylcylotetrasiloxane and decamethylcyclopentasiloxane, as part of the oils blended therein.

Friction and water, etc., are external factors which impair makeup retention. To improve poor makeup retention which occurs due to water-soluble substances, such as sweat and tears, loss of water-soluble components and sebum, etc., in the skin is prevented, and the protective effect of the skin is maintained, by blending with silicone oils to increase water repellent properties.

For example, since they have the characteristic features of light feel, outstanding water-repellent properties and high safety, silicone oils such as dimethylpolysiloxane are being used profusely in makeup oils in recent years.

Pigments such as red ocher and titanium oxide, etc. and powders such as mica and sericite are widely used in makeup or antiperspirant such as lipstick, lip balm, nail varnish, nail coat, foundation, mascara or eyeliner, and in order to impart sufficient water repellent properties and sufficient safety to these materials, it is common to perform a surface treatment by metallic soap, alumina, silica, phosphating, etc.

For example, in U.S. Pat. No. 2,719,303, a method is disclosed of carrying out surface treatment with 12–60 weight parts of methyl hydrogen polysiloxane to 100 weight parts of powder. In Provisional Publication No. 7-196946, a surface treatment method is disclosed using a straight chain single-terminated alkoxy denatured silicone. These powder treatments with silicone are generally known in the art, but enhanced miscibility with ordinary oils, enhanced miscibility with fluorinated oils, enhanced miscibility with silicone oils or improved stability of emulsions in these composite systems, was desired.

Means for Solving the Problems

The main object of this invention is a silicone compound represented by the general formula (1):

$$R^1{}_a R^2{}_b R^3{}_c SiO_{(4-a-b-c)/2}$$

(in the formula, $R^1$ is at least one organic group having 1–30 carbon atoms chosen from alkyl, aryl, aralkyl, fluorine-substituted alkyl or organopolysiloxanylsilyl, $R^2$ is a reactive substituent group chosen from hydrogen, hydroxy or alkoxy having 1–6 carbon atoms, or a reactive substituent group in which at least one of carbon, oxygen and silicon are bonded to these reactive substituent groups, $R^3$ is a carboxylate residue represented by the following general formula (2):

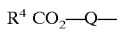

$R^4$ is a saturated or unsaturated hydrocarbon group having 2–30 carbon atoms, Q is a bivalent hydrocarbon group which may also contain a hetero atom, a is 1.0–2.5. b is 0.001–1.5, and c is 0.001–1.5.

Another object of this invention is the above-mentioned silicone compound wherein $R^3$ is a carboxylate residue represented by the general formula (3):

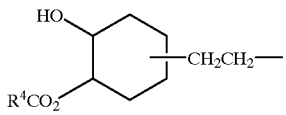

(in the formula, $R^4$ is a saturated or unsaturated hydrocarbon group having 2–30 carbon atoms).

Another object of this invention is the above-mentioned silicone compound wherein $R^4$ is a resin acid residue of a tricyclic diterpene carboxylic acid.

Another object of this invention is the above-mentioned silicone compound wherein at least part of $R^1$ is represented by the following general formula (4):

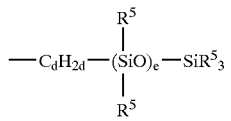

in the formula, $R^5$ may respectively be identical or different, and is at least one substituent group having 1–30 carbon atoms chosen from alkyl, aryl, aralkyl, fluorine-substituted alkyl or hydroxyl, d is 1–5, and e is 0–500).

Another object of this invention is a method of manufacturing the above-mentioned silicone compound comprising the synthesis of an alicyclic epoxy-modified silicone by an addition reaction of a main chain siloxane which is an organohydrogen polysiloxane to a vinyl alicyclic epoxide, and the reaction of a saturated or unsaturated carboxylic acid therewith.

EXAMPLES

The silicone compound used in this invention is represented by the following general formula (1):

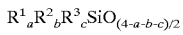

In the formula, $R^1$ is at least one organic group having 1–30 carbon atoms chosen from alkyl, aryl, aralkyl, fluorine-substituted alkyl or organopolysiloxanylsilyl. $R^1$ may be an alkyl group such as methyl, ethyl, propyl, butyl, pentyl, hexyl, heptyl octyl, nonyl or decyl; a cycloalkyl group such as cyclopentyl or cyclohexyl; an aryl group such as phenyl or tolyl; an aralkyl group such as benzyl or phenetyl; an alcohol residue such as olioxy or alioxy; a fluorinated alkyl group such as trifluoropropyl or heptadeca-fluorodecyl, and organopolysiloxanylsilyl alkyl represented by the following general formula (4):

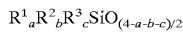

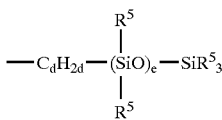

It is preferable that at least about 80% of $R^1$ are methyl groups. Moreover, it is preferable that at least part of $R^1$ is the organopolysiloxanylsilyl alkyl group represented by the above-mentioned general formula (4). In the above formula (4), $R^5$ may respectively be identical or different, and comprise at least one substituent group having 1–30 carbon atoms chosen from alkyl, aryl, aralkyl, fluorine-substituted alkyl or hydroxyl, and d is 1–5. In particular, when synthesizing this substituent from the reaction of a vinyl group and a SiH group, d is 2, and e is 0–500, but preferably 1–100.

When e is larger than 500, problems such as poor reactivity of the main chain may arise.

The silicone compound represented by the general formula (1) is synthesized by an equilibrium reaction using an acid or alkali catalyst according to standard methods. The branch silicone unit in this silicone compound is introduced by using a trialkoxymethylsilane, trihydroxymethylsilane, tris(trimethylsiloxy)methylsilane and their straight chain or cyclic polymers for the equilibrium reaction, or branched by performing a ring opening polymerization with a living polymerization catalyst using a silanol-denatured silicone.

The silicone which is branched by the organopolysiloxanylalkyl group shown by the general formula (4) can be synthesized by an addition reaction of an organohydrogen polysiloxane to a single-terminated vinyl-denatured organopolysiloxane or vinyl-denatured organosilane represented by the following general formula (5):

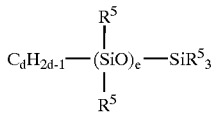

(in the formula, $R^5$ is the same as that of the above-mentioned definition).

$R^2$ is at least one reactive substituent group chosen from hydrogen, hydroxy or alkoxy having 1–6 carbon atoms, e.g., methoxy, ethoxy and isopropenoxy, or a reactive substituent group in which at least one group containing carbon, oxygen and silicon (e.g., alkylene, alkylene ether) is bonded to these reactive substituent groups.

These reactive substituents can be introduced by carrying out an addition reaction of vinyl trichlorosilane, vinyltris(beta methoxyethoxy)silane, vinyltri methoxysilane and vinyltriethoxy silane to a SiH group. In particular, when used for cosmetic purposes, unreacted methoxy groups, the methanol of the SiH group and hydrogen, etc., pose a problem, so it is preferred that this reactive substituent includes a hydroxy group or an ethoxy group. It may be monofunctional or trifunctional, as for example in dimethylethoxysilyl, diethoxymethylsilyl and triethoxysilyl.

$R^3$ is a carboxylate residue represented by the following general formula (2).

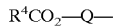

In the formula, $R^4$ is a saturated or unsaturated hydrocarbon group having 2–30 carbon atoms, preferably a resin acid residue such as acetic acid, butyric acid, capric acid, lauric acid, myristic acid, palmitic acid, stearic acid, behenic acid, melissic acid, palmitoleic acid, oleic acid, linolic acid, linolenic acid, arachidonic acid, erucic acid, 2-ethyl hexanoic acid, 2-hexyl decanoic acid, 2-heptyl undecanoic acid, 5,7,7-trimethyl-2-(1,3,3-trimethylbutyl)octanoic acid, methyl branched isostearic acid, cyclopentane carboxylic acid, cyclohexane carboxylic acid, cholic acid, deoxycholic acid, glycyl lysine acid, benzoic acid, naphthoic acid, undecylenic acid or a tricyclic diterpene carboxylic acid. Of these, resin acid residues such as tricyclic diterpene carboxylic acid, undecylenic acid which is a solid at ordinary temperature, stearic acid or erucic acid are to be preferred, and resin acid residues of tricyclic diterpene carboxylic acids are still more preferred. As the resin acid residue of a tricyclic diterpene carboxylic acid, the resin acid residue of rosin or hydrated rosin is preferable. It may also be at least one carboxylic acid residue chosen from abietic acid, neoabietic acid, dihydroabietic acid, d-pimaric acid, iso d-pimaric acid, dihydroabietic acid, levopimaric acid, palustric acid, dextropimaric acid, sandarachpimaric acid, and their hydrates.

In the above-mentioned general formula (2), Q is a bivalent hydrocarbon group and may also contain a hetero atom. $R^3$ may for example be a bivalent hydrocarbon group or polyoxyalkylene group such as $R^4CO_2$—$(CH_2)p$-, $R^4CO_2$—$(C_2H_4O)_p(CH_2)_q$—, $R^4CO_2$—$(C_3H_6O)_p(CH_2)_q$—, $R^4CO_2$—$(C_2H_4O)_p(C_3H_6O)_q(CH_2)_r$—(in the formula, p, q, and r are integers), or a cyclic hydrocarbon group represented by the following general formula (3) (in the formula, $R^4$ is the same as that of the above-mentioned definition.)

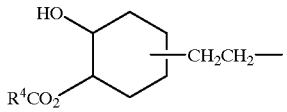

Also, a=1.0–2.5 but preferably 1.2–2.3, and b=0.001–1.5 but preferably 0.05–1.0. When b is less than 0.001, the reactivity with the powder is low. c=0.001–1.5, and preferably 0.05–1.0.

Although there is no limit to the weight average molecular weight when using the silicone compound of the above-mentioned general formula (1) as a surface treatment agent for a powder, it is preferably 300–100000 and more preferably 1000–10000. If 100000 is exceeded, it gives a tacky feel due to the viscosity of silicone, and when it is less than 300, the smoothness which is the characteristic feature of silicone may not be obtained.

Although there is no particular limit to the powder of this invention if it is a powder generally used for makeup, black iron oxide, titanium oxide, talc, mica, red ocher, yellow iron oxide, chrome oxide, ultramarine blue, titanium-coated mica, sericite, processed talc, particulate titanium oxide, mica titanium, particulate zinc oxide and zinc oxide are preferable. Zinc oxide, titanium oxide, mica and sericite are particularly preferable.

The silicone compound represented by the above-mentioned general formula (1) may be easily synthesized by carrying out an addition reaction of an organohydrogen polysiloxane, the vinyl carboxylate represented by the following general formula (6):

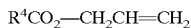

and a terminally reactive alkalene compound in the presence of a platinum catalyst or rhodium catalyst (in the formula, $R^4$ is the same as that of the above.)

Moreover, this silicone compound may also be synthesized by synthesizing an alicyclic epoxy-modified silicone by the addition reaction of a main chain siloxane which is an organohydrogen polysiloxane to an alicyclic epoxide according to the following reaction equation (7):

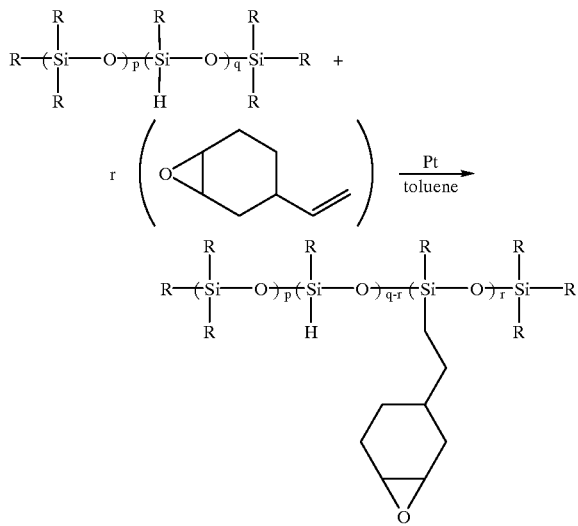

adding other silicone compounds if needed, and reacting saturated or unsaturated carboxylic acids, especially tricyclic diterpene carboxylic acid (abbreviated as X-COOH in the following reaction) according to reaction equation (8):

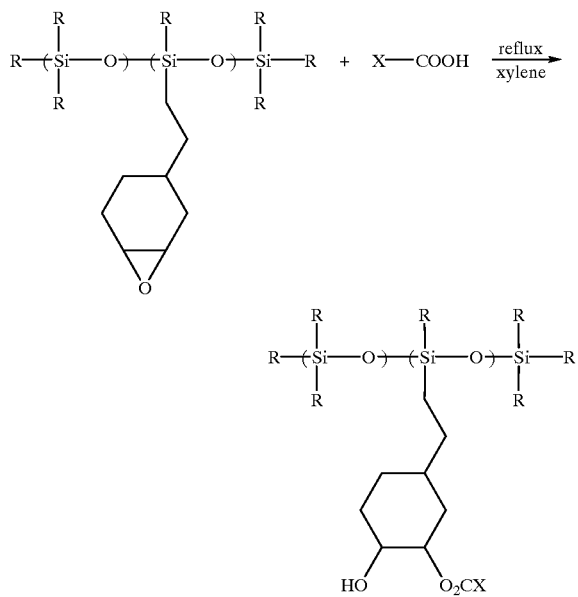

The addition reaction of the hydrogen silicone compound and the alicyclic epoxide of reaction equation (7) may easily be carried out in the presence of a platinum catalyst or rhodium catalyst. The reaction of the alicyclic epoxy-modified silicone and carboxylic acid of reaction equation (8) does not require a catalyst, and can be carried out simply by heating. In this case, the reactive substituent may be introduced to the silicone main chain either in the synthesis of the alicyclic epoxy-modified silicone, or after the reaction of the alicyclic epoxy-modified silicone and carboxylic acid. However, as the reaction of the alicyclic epoxy-modified silicone and carboxylic acid is performed at high temperature, it is preferable to introduce the reactive substituent after the reaction of the alicyclic epoxy-modified silicone and carboxylic acid.

Here, although the organohydrogen polysiloxane may be straight chain or cyclic, it is preferable that it is straight chain as addition reactivity is good, moreover, the bonding site of the SiH group may be either the side chain or the terminal.

The mixing ratio of organohydrogen polysiloxane, terminally-reactive alkylene compound, silicone compound represented by the above-mentioned general formula (5), and vinyl carboxylate represented by the above-mentioned general formula (6), expressed as the mole ratio of terminal unsaturated groups to SiH groups, may be set to 0.2–2.0, but if unreacted SiH groups remain, evolution of hydrogen gas will occur which is undesirable, so the ratio is preferably 0.5–1.2.

The above-mentioned addition reaction is preferably performed in the presence of a platinum catalyst or a rhodium catalyst, suitable examples being chloroplatinic acid, alcohol-denatured chloroplatinic acid and chloroplatinic acid-vinyl siloxane complex, etc. The catalyst usage amount can be taken as the catalyst amount, which in terms of platinum or rhodium amount is 50 ppm or less, but more preferably 20 ppm or less. The above-mentioned addition reaction may be performed in an organic solvent if necessary. Examples of this organic solvent are aliphatic alcohols such as methanol, ethanol, 2-propanol, and butanol, aromatic hydrocarbons such as toluene and xylene, aliphatic or aromatic hydrocarbons such as n-pentane, n-hexane and cyclohexane, or halogenated hydrocarbons such as dichloromethane, chloroform and carbon tetrachloride. The conditions of the above-mentioned addition reaction are not limited, but the reaction may conveniently be carried out under reflux for 1 to 10 hours.

The aforesaid reaction of the epoxy group and carboxylic acid is simply completed by heating at 60–200 degrees C in an organic solvent. Although an acid catalyst can also be used as a catalyst as it promotes the reaction, a catalyst is not required if an alicyclic epoxy group is used as in this invention. As organic solvents, aromatic hydrocarbons such as toluene and xylene which have a high boiling point may particularly be mentioned. This reaction may conveniently be carried out under reflux for 1 to 20 hours.

Although the silicone compound of this invention can be used for various intended uses, it is especially suitable as a surface treatment agent for a powder. In this case, the blending ratio of the silicone compound of above-mentioned general formula (1) and the powder is 0.1–30 weight parts, but preferably 0.5–10 weight parts, per 100 weight parts of powder.

The novel silicone powder treatment agent of this invention can be used to treat a powder surface by well-known methods. For example, the following methods may conveniently be used.

1. Dispersion of powder to be treated in water or organic solvent containing the powder treatment agent.
2. Mixing powder and powder treatment agent, followed by surface treatment method using trituration machines, such as a ball mill or jet mill.
3. Blending the silicone oil (particularly methylhydrogen polysiloxane or methyl hydroxy polysiloxane) with a solvent, dispersing the powder to coat the surface, drying and sintering.

The makeup of this invention comprises a) a powder which is surface-treated by the silicone compound of this invention, and b) a compound containing alcoholic hydroxyl groups. It may also contain c) oil and/or d) water. An excellent makeup may be obtained from a) a powder which is surface-treated by the silicone compound of this invention, b) a compound containing alcoholic hydroxyl groups and c) oil and/or d water, but e) powders (powders other than the powder surface-treated by the silicone compound of this invention) and/or colorants, f) surfactants, g) cross-linked organopolysiloxanes and h) silicone resins, such as acryl/silicone graft or block copolymer, and silicone lattice compounds, etc., may also be added if necessary.

The blending proportion of the makeup of this invention differs depending on the type and form of the target product, but in general, the powder which is surface-treated by the above-mentioned silicone compound may be blended in a proportion of 0.1 to 99.9% weight parts relative to the whole product.

Examples of the compound b) having an alcoholic hydroxyl group in the molecule, which is a compositional component of this invention, are the following.

Alcohols which can be added include lower alcohols, such as ethanol and isopropanol; and sugar alcohols, such as sorbitol and maltose. Examples of sterols are cholesterol, sitosterol, phytosterol and lanosterol.

Water-soluble polymers which can be added include vegetable polymers, such as gum arabic, tragacanth, galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride.

In these water-soluble polymers, film-forming agents, such as polyvinyl alcohol and polyvinyl pyrrolidine, may also be included.

One or more kinds of these materials may be used as necessary. Of these, water-soluble, univalent or polyhydric alcohols, or their mixtures, are preferable, and water macromolecules are particularly preferable.

The content of the compound b) which has an alcoholic hydroxyl group in its molecular structure in the makeup of this invention is 0.1 to 99.9 weight %, and preferably 0.5–50.0 weight %. If the content is less than 0.5 weight %, moisturizing properties, antibacterial properties and antibiological properties, which are the effects of compounds containing an alcoholic hydroxyl group in its molecular structure, are inadequate, and if 50 weight % is exceeded, the effect of the silicone compound of this invention may not be forthcoming.

The following are examples of the oil c) which is a compositional component of this invention.

Natural animal and vegetable fats and oils, but also semi-synthetic fats and oils, including avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, beeds wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil. (Additionally, the term "POE" as used herein stands for polyoxyethylene).

Examples of hydrocarbon oils include ozokerite, squalane, squalene, ceresine, paraffin, paraffin wax, liquid paraffin, pristane, polyisobutylene, microcrystalline wax and Vaseline; and those of a higher fatty acid which can be mixed include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oils include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester, diisostearyl malic acid, dextrin palmitic acid ester, dextrin stearic acid ester, dextrin 2-ethylhexanic acid palmitic acid ester cane sugar palmitic acid ester, cane sugar stearic acid ester, monobenzylidene sorbitol and dibenzylidene sorbitol.

Examples of glyceride oils include acetoglyceride, diisooctanoic acid glyceride, triisostearic acid glyceride, triisopalmitic acid glyceride, tri-2-ethylhexanoic acid glyceride, monostearic acid glyceride, di-2-heptylundecanoic acid glyceride and trimyristic acid glyceride.

As examples of silicone oils, mention may be made of higher alkoxy-modified silicones such as dimethylpolysiloxane, methylphenyl-polysiloxane, methylhydrogenpolysiloxane, octamethylcyclotetrasiloxane, decamethylcyclopentasiloxane, dodecamethylcyclohexasiloxane, tetramethyltetrahydrogencyclotetrasiloxane and stearoxysilicone, higher fatty acid-modified silicones, fluorine-modified silicones, amino-modified silicones, alkyl-modified silicones, higher fatty acid ester-modified silicones, silicone resins and silicone rubbers.

As examples of fluorine-containing oils, mention may be made of perfluoropolyether, perfluorodecalin and perfluorooctane.

One of more of these may be used as necessary.

It is preferred that these oils are liquid at ordinary temperature, more preferable that they are organic powders having a silicone resin and/or silicone elastomer skeleton with a structural repeating unit of —[O—Si—] n-, and still more preferable that these powders comprise, at least partially, a fluorine group or an amino group.

The content of the oil c) in the makeup of this invention is 0–90 weight %, and preferably 1–90 weight %. If this content is less than 1% of the weight, it is difficult to manufacture the makeup mold of this invention, and if 90% is exceeded, the effect of the silicone compound of this invention cannot be obtained.

The makeup of this invention may also contain d) water. The content of water in the makeup of this invention is 0–99.0 weight %, which may be increased or decreased according to the form of the makeup.

The following may be mentioned as examples of the e) powder and/or the colorant of this invention. Here, the term "powder" refers to powders other than the powder which is surface-treated by the silicone compound of this invention.

Examples of a usable inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calciumsecondary phosphate, alumina, aluminum hydroxie, boron nitride and silica.

Examples of a usable organic powder include polyamide powder, polyester powder, polyethylene powder, polypropylene powder, polystyrene powder, polyurethane powder, benzoguanamine powder, polymethylbenzoguanamine powder, polytetrafluoroethylene powder, polymethylmethacrylate powder, cellulose powder, silk powder, nylon powder such as 12-nylon powder or 6-nylon powder, silicone powder, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder, polycarbonate resin powder, microcrystalline fiber powder, starch powder and lauroyl lysine powder.

Examples of a usable surfactant metal salt powder (metal soap powder) include powders of zinc stearate, aluminum stearate, calcium stearate, magnesium stearate, zinc myristate, magensium myristate, zinc cetylphosphate, calcium cetylphosphate and zinc sodium cetylphosphate.

Examples of a usable colored pigment include inorganic red pigments, such as iron oxide, iron hydroxide and iron titanate; inorganic brown pigments, such as (gamma-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powder complexes of the inorganic pigments mentioned above.

Examples of a usable pearl pigment include titanium oxide-coated mica, bismuth oxychloride, titanium oxide-coated bismuth oxychloride, titanium oxide-coated talc, fish scales, and titanium oxide-coated colored mica; and examples of a usable metallic powder pigment include aluminum powder, copper powder and stainless powder.

Examples of a usable tar pigment include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207 (according to the pigment nomenclature method in JIS); and examples of a usable natural pigment include powders of carminic acid, laccaic acid, carthamin, bradilin and crocin.

The present silicone compounds are applicable to surface treatment of any powders so far as the powders can be used in general cosmetic materials, irrespective of their shape (whether it is spherical, acicular or tabular), their size (whether it is fume, fine grain or pigment), and their structure (whether it is porous or nonporous). It is preferred that part or all of the powder and/or colorant is an organic powder having a silicone resin and/or silicone elastomer skeleton with a structural repeating unit of —[O—Si—] n-. These powders may also be complexed and/or surface-treated with an oil, silicone or fluoride compound.

Furthermore, the present cosmetic materials can contain one or more surfactants, if desired.

Examples of a usable anionic surfactant include saturated or unsaturated fatty acid soap such as sodium stearate or triethanolamine palmitate; alkyl ether carboxylic acids and salts thereof; salts of amino acid-fatty acid condensates; amido ether carboxylic acid salts; alpha-sulfo fatty acid esters, alpha-acyl sulfonic acid; alkylsulfonic acids; alkene-sulfonic acids; sulfonated fatty acid esters; sulfonated fatty acid amides; sulfonates of alkyl sulfonic acid salts and their formaldehyde condensates; alkyl sulfonic acid ester salts; secondary alcohol sulfates; alkyl and aryl ether sulfates; fatty acid ether sulfates, fatty acid alkylolamide sulfates; sulfate esters such as Turkey red oil; alkyl phosphates; alkenyl phosphates; ether phosphates; alkyl aryl ether phosphates; alkylamide phosphates; and active agents of N-acylamino acid type.

Examples of a usable cationic surfactant include amine salts, such as alkylamine salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopoly-siloxanes, organopolysiloxanes modified with both polyoxyalkylene and alkyl groups, alkanolamides, sugar ethers and sugar amides.

Examples of a usable amphoteric surfactant include betaine, aminocarboxylates and imdazoline derivatives.

These surfactants are preferably modified silicones having a polyoxyalkylene chain in the molecule, and the HLB (hydrophilic lipid balance) of these surfactants is preferably 2–8.

The g) cross-linked organopolysiloxanes suitable for the present cosmetic materials are those which cause swelling when they contain a silicone having low viscosity of from 0.65 to 10.0 cs in a quantity larger than their self weight. It is desirable that the cross-linked structure of those organopolysiloxanes be formed by reaction between the hydrogen atoms bonded directly to silicon atoms and a cross-linking agent having at least two vinylic reactive moieties per molecule. Further, it is desirable in the foregoing reaction to use a cross-linking agent containing at least one moiety selected from polyoxyalkylene, alkyl, alkenyl, aryl and fluoroalkyl moieties.

It is preferred that the h) silicone resins of this invention, such as acryl/silicone graft or block copolymers and silicone compounds having a lattice structure, are acryl silicones. It is moreover preferred that the silicone resins of this invention are acryl silicones containing at least one moiety selected from the group consisting of pyrrolidone, long-chain alkyl, polyoxyalkylene and fluoroalkyl moieties. The other favorable silicone resins are silicone compounds having a lattice structure.

There is no particular limitation on the applications of the makeup of this invention, but examples include skin care products, hairdressing products, antiperspirant, makeup products and ultraviolet defense products. There is also no particular limitation on the form of the product, but it may be applied to liquid, emulsion, cream, solid, paste, gel, powder, laminate, mousse and spray.

EXAMPLES

Example 1

Synthesis of Silicone 1

708 weight parts of organohydrogensiloxanes represented by the following average structural formula (9):

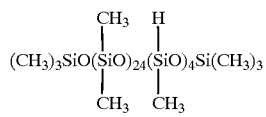

1,000 weight parts of isopropyl alcohol and 455 weight parts of a vinyl hydrated rosin compound represented by the following structural formula (10):

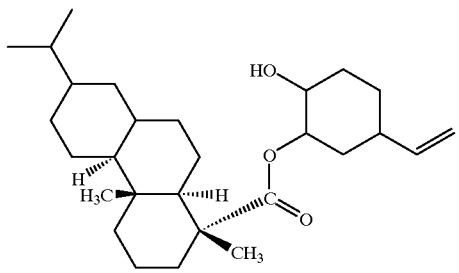

were placed in a reaction vessel, 2 weight parts of a 0.5 weight % isopropyl alcohol solution of chloroplatinic acid was added thereto, and the reaction was carried out for 6 hours under reflux of the solvent.

The reaction was continued for 6 hours under reflux of the solvent while dripping 76 weight parts of vinyl triethoxysilane into the reaction vessel. The reaction mixture was heated under reduced pressure to distill off the solvent therefrom, and an organopolysiloxane represented by the following average empirical formulae (11), (12):

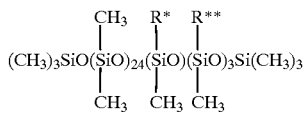

was thereby obtained (in the formula, $R^* = $—$C_2H_4Si(OEt)_3$,

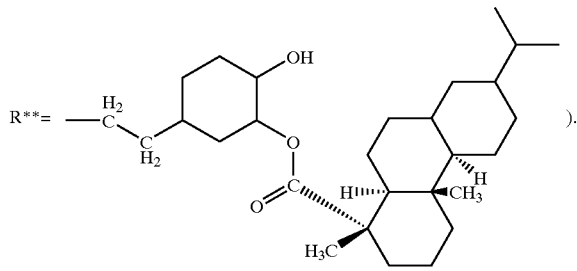

).

This product was a light brown transparent liquid, viscosity 14600 cs (25° C.), specific gravity 1.020 (25° C.) and refractive index 1.453.

Example 2

Synthesis of Silicone 2

708 weight parts of organohydrogensiloxanes represented by the following average empirical formula (13):

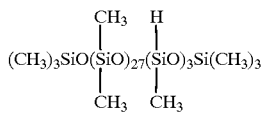

1,000 weight parts of isopropyl alcohol and 300 weight parts of a vinyl hydrated rosin compound were placed in a reaction vessel, 2 weight parts of a 0.5 weight % isopropyl alcohol solution of chloroplatinic acid was added thereto, and the reaction was carried out for 6 hours under reflux of the solvent.

The reaction was continued for 6 hours under reflux of the solvent while dripping 76 weight parts of vinyl triethoxysilane into the reaction vessel. The reaction mixture was heated under reduced pressure to distill off the solvent therefrom, and an organopolysiloxane represented by the following average empirical formula (14):

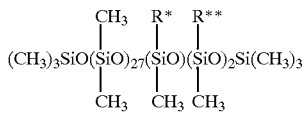

was thereby obtained (in the formula, R* and R** have the same significance as above).

This product was a light brown transparent liquid, viscosity 1200 cs (25° C.), specific gravity 1.003 (25° C.) and refractive index 1.428.

Example 3

Synthesis of Silicone 3

600 weight parts of organohydrogensiloxanes represented by the following average empirical formula (15):

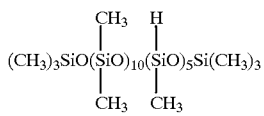

1,000 weight parts of toluene and 260 weight parts of a pentamethylvinyl siloxane were placed in a reaction vessel, 2 weight parts of a 0.5 weight % toluene solution of chloroplatinic acid was added, and the reaction was carried out for 6 hours under reflux of the solvent.

The reaction was continued for 6 hours under reflux of the solvent while dripping 120 weight parts of vinyl triethoxysilane into the reaction vessel. The reaction mixture was heated under reduced pressure to distill off the solvent therefrom, and an organopolysiloxane represented by the following average empirical formula (16):

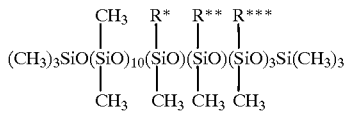

was thereby obtained (in the formula, R* and R** have the same significance as above,

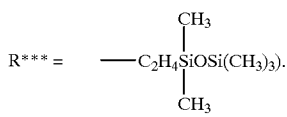

This product was a light brown transparent liquid, viscosity 57cs (25° C.), specific gravity 0.958. (25° C.).

Example 4

Manufacture of Powder Foundation 98 weight parts of a titanium oxide powder heat-treated beforehand by reduced pressure drying was introduced into a reaction vessel, and a solution of 2 weight parts of the silicone 1 synthesized in Example 1 diluted in toluene was gradually added with stirring. The temperature was increased to distil off the toluene, and baking performed with agitation at 150° C. for 3 hours. The powder was returned to room temperature in a current of nitrogen, and siliconized titanium oxide thereby obtained. Next, the same treatment was performed using sericite instead of this titanium oxide, and siliconized sericite thereby obtained.

A powder foundation was manufactured by processing the ingredients below according to the following process.

| Ingredient | Proportion (weight %) |
|---|---|
| (1) Above-mentioned siliconized titanium oxide | 12.0 |
| (2) Above-mentioned siliconized sericite | 35.0 |
| (3) Lecitin-treated talc | 35.1 |
| (4) Lecitin-treated spherical nylon powder | 5.0 |
| (5) Red ocher | 0.4 |
| (6) Yellow iron oxide | 2.0 |
| (7) Amber | 0.4 |
| (8) Black iron oxide | 0.1 |
| (9) Dimethylpolysiloxane (6 cs) | 7.0 |
| (10) Glyceryl trioctanic acid | 1.5 |
| (11) Dipentaerythritol fatty acid ester | 1.5 |

Manufacturing Method

Step 1: Components (1)–(8) are mixed and uniformly pulverized.

Step 2: Components (9)–(11) are added, pulverized, and press-molded to give a powder foundation.

The foundation obtained was evaluated by 50 female panelists according to the criteria shown in Table 1 below as to usability, makeup retention, spreading ability and absence of blotches.

TABLE 1

| Score | Usability/makeup holding power | Spread | Absence of stains |
|---|---|---|---|
| 5 points | good | light | good |
| 4 points | fair | fairly light | fairly good |
| 3 points | normal | normal | normal |
| 2 points | rather poor | rather heavy | rather poor |
| 1 points | poor | heavy | poor |

The average marks in the evaluation of these 50 female panelists were determined by Ox for each example on the following basis.

Evaluation of Average Marks

Average mark was 4.5 points or higher. ⊚

Average mark was above 3.5 points and less than 4.5 points. ○

Average mark was above 2.5 points and less than 3.5 points. Δ

Average mark was above 1.5 points and less than 2.5 points. x

Average mark was less than 1.5 points. XX

Example 5

Manufacture of Powder Foundation

A powder foundation was manufactured in the same way as in Example 4 using the silicone 2 synthesized in Example 2 instead of the silicone 1, and an evaluation was performed.

Comparative Example 1

Manufacture of Powder Foundation

A powder foundation was manufactured in the same way as in Example 4 using KF99 (methylhydrogen polysiloxane, Shin-Etsu Chemicals, Inc.) instead of the silicone 1, and an evaluation was performed.

Comparative Example 2
Manufacture of Powder Foundation

A powder foundation was manufactured in the same way as in Example 4 using the silicone compound represented by the following empirical formula (18):

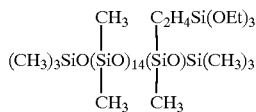

instead of the silicone 1.

The test results for Examples 4, 5 and Comparative Examples 1, 2 are shown in Table 2.

TABLE 2

|  | Example 4 | Example 5 | Comparative Example 1 | Comparative Example 2 |
|---|---|---|---|---|
| Ease of use | ⊚ | ○ | Δ | Δ |
| Light spread | ⊚ | ⊚ | ○ | Δ |
| Absence of blotches | ○ | ⊚ | Δ | Δ |
| Makeup retention | ⊚ | ⊚ | ○ ~ Δ | Δ ~ x |

As can be seen from Table 2, the foundations of Examples 4 and 5 had a light spread, were easy to use and gave no blotches compared to Comparative Examples 1 and 2, while makeup retention was also good. It was also observed that in the case of Comparative Example I where the powder was processed by KF99, the container swelled up during closed storage as a result of a dehydrogenation reaction by unreacted Si—H groups.

Example 6
Manufacture of Eyeliner 99 parts of black iron oxide powder which had previously been heat-treated by pressure reduction and drying was introduced into a reaction vessel, and a solution comprising the silicone 1 (1 part) obtained in Example 1 diluted in toluene was gradually added with stirring. The temperature was then raised to distil off the toluene, and the product was baked with stirring for 3 hours at 150° C. The powder was returned to room temperature in a current of nitrogen, and used.

Next, an eyeliner was manufactured by processing the ingredients below according to the following process.

| Ingredient | Proportion (weight %) |
|---|---|
| 1. Decamethylcyclopentasiloxane | 45.0 |
| 2. Polyether-denatured siloxane (Shin-Etsu Chemical Co., Ltd., KF-6017) | 3.0 |
| 3. Organic silicone resin | 15.0 |
| 4. Dioctadecyldimethylammonium salt denatured montmorillonite | 3.0 |
| 5. Black iron oxide processed with silicone 1 | 10.0 |
| 6. 1, 3-butylene glycol | 5.0 |
| 7. Sodium dehydroacetate | Suitable amount |
| 3. Antiseptics | Suitable amount |
| 9. Perfume | Suitable amount |
| 10. Purified water | Remainder |

Manufacturing Method

Step A: Components 1–4 are mixed, component 5 is added, and the mixture uniformly blended and dispersed.

Step B: Components 6–8 and 10 are blended.

Step C: After gradually adding the mixture obtained in step B to the mixture obtained in step A, and emulsifying it, component 9 was added to obtain the eyeliner.

The eyeliner obtained had a light spread, was easy to draw, and had a cool and clean feel without stickiness. It also showed no change with respect to temperature or time, excellent stability in use, excellent water resistance and antiperspirant properties, and had very good makeup retention.

Example 7
Manufacture of Foundation 99 parts each of titanium oxide, talc, mica, red ocher, and yellow and black iron oxide powder which had previously been heat-treated by pressure reduction and drying, were introduced into a reaction vessel, and a solution comprising the silicone 1 (1 part) obtained in Example 1 diluted in toluene was gradually added with stirring. The temperature was then raised to distil off the toluene, and the product was baked with stirring for 3 hours at 150° C. The powder was returned to room temperature in a current of nitrogen, and used.

Next, a foundation was manufactured by processing the ingredients below according to the following process.

| Ingredient | Proportion (weight %) |
|---|---|
| 1. Decamethylcyclopentasiloxane | 45.0 |
| 2. Dimethylpolysiloxane (6 cs) | 5.0 |
| 3. Polyether denatured silicone (Shin-Etsu Chemical Co., Ltd., KF-6017) | 2.0 |
| 4. Octadecyldimethylbenzyl aluminium salt denatured montmorillonite | 4.0 |
| 5. Titanium oxide treated with silicone 1 | 10.0 |
| 6. Talc treated with silicone 1 | 6.0 |
| 7. Mica treated with silicone 1 | 6.0 |
| 8. Red ocher treated with silicone 1 | 1.6 |
| 9. Yellow iron oxide treated with silicone 1 | 0.7 |
| 10. Black iron oxide treated with silicone 1 | 0.2 |
| 11. Dipropylene glycol | 5.0 |
| 12. Paraoxybenzoic acid methyl ester | 0.3 |
| 13. 2-amino-2-methyl -1, 3-propanediol | 0.2 |
| 14. Hydrochloric acid | 0.1 |
| 15. Perfume | Suitable amount |
| 16. Water | Remainder |

Manufacturing Method

Step A: Components 1–4 are mixed, component 5 is added, and the mixture uniformly blended and dispersed.

Step B: Components 6–8 and 10 are blended.

Step C: After gradually adding the mixture obtained in step B to the mixture obtained in step A, and emulsifying it, it was cooled and component 16 was added to obtain the foundation.

The foundation obtained was fine, easy to spread, no stickiness or oiliness, and had a cool, fresh feel. Makeup retention was also good, there was no change with respect to temperature or time, and it was very stable.

Example 8
Manufacture of Eye Shadow 99 parts each of chromium oxide, ultramarine blue and titanium-coated mica which had previously been heat-treated by pressure reduction and drying, were introduced into a reaction vessel, and a solution comprising the silicone 1 (1 part) obtained in Example 1 diluted in toluene was gradually added with stirring. The temperature was then raised to distil off the toluene, and the product was baked with stirring for 3 hours at 150° C. The powder was returned to room temperature in a current of nitrogen, and used.

Next, an eye shadow was manufactured by processing the ingredients below according to the following process.

| Ingredient | Proportion (weight %) |
|---|---|
| 1. Decamethylcyclopentasiloxane | 15.0 |
| 2. Dimethylpolysiloxane (6 cs) | 5.0 |
| 3. Polyether denatured silicone (polyoxyalkylene/alkyl denatured organopolyoxysiloxane, (Shin-Etsu Chemical Co., Ltd., KF-6017) | 2.0 |
| 4. PEG(10) uraryl ether | 0.5 |
| 5. Chromium oxide treated with silicone 1 | 6.2 |
| 6. Ultramarine blue treated with silicone 1 | 4.0 |
| 7. Titanium-coated mica treated with silicone 1 | 6.0 |
| 8. Sodium chloride | 2.0 |
| 9. Propylene glycol | 8.0 |
| 10. Antiseptics | Suitable amount |
| 11. Perfume | Suitable amount |
| 12. Purified water | Remainder |

Manufacturing Method

Step A: Components 1–4 are mixed, components 5–7 are added, and the mixture uniformly dispersed.

Step B: Components 8–10 and 12 are homogeneously dissolved.

Step C: After gradually adding the mixture obtained in step B to the mixture obtained in step A and emulsifying it with stirring, component 11 was added to obtain the eye shadow.

The eyeliner obtained had a light spread without being oily or powdery, and felt fresh and clean. It also had excellent water resistance and water repellent properties, good antiperspirant properties and good retention.

Makeup based on it did not become messy, it showed no change with respect to temperature or time, and it was very stable.

Example 9

Manufacture of Liquid Emulsion Foundation 99 parts each of titanium oxide, sericite, treated talc, red ocher, and yellow iron oxide and black iron oxide powders which had previously been heat-treated by pressure reduction and drying, were respectively introduced into a reaction vessel, and a solution comprising the silicone 2 (1 part) obtained in Example 2 diluted in toluene was gradually added with stirring. The temperature was then raised to distil off the toluene, and the product was baked with stirring for 3 hours at 150° C. The powder was returned to room temperature in a current of nitrogen, and used.

Next, a liquid emulsion foundation was manufactured by processing the ingredients below according to the following process.

| Ingredient | Proportion (weight %) |
|---|---|
| 1. Dimethylpolysiloxane (6 cs) | 5.0 |
| 2. Decamethylcyclopentasiloxane | 15.0 |
| 3. Squalane | 4.0 |
| 4. Neopentyl glycol diooctanate | 3.0 |
| 5. Isostearic acid diglyceride myristate | 2.0 |
| 6. Alpha-monoisostearyl glyceryl ether | 1.0 |
| 7. Polyether denatured silicone (polyoxyalkylene/ alkyl denatured organopolysiloxane, Shin-Etsu Chemical Co., Ltd., KF6026) | 1.0 |
| 8. Aluminum distearate | 0.2 |
| 9. Titanium oxide treated with silicone 2 | 5.0 |
| 10. Sericite treated with silicone 2 | 2.0 |
| 11. Talc treated with silicone 2 | 3.0 |
| 12. Red ocher treated with silicone 2 | 0.4 |
| 13. Yellow iron oxide treated with silicone 2 | 0.7 |
| 14. Black iron oxide treated with silicone 2 | 0.1 |
| 15. Magnesium sulfate | 0.7 |
| 16. Glycerol | 3.0 |
| 17. Antiseptics | Suitable amount |
| 18. Perfume | Suitable amount |
| 19. Purified water | Remainder |

Manufacturing Method

Step A: Components 1–8 are mixed, components 9–15 are added, and the mixture uniformly dispersed.

Step B: Components 16–17 and 19 are dissolved by heating.

Step C: After gradually adding the mixture obtained in step B to the mixture obtained in step A and emulsifying it with stirring, the product was cooled, and component 18 was added to obtain the liquid emulsion foundation.

The liquid emulsion foundation obtained had a low viscosity, fineness, a light spread without being sticky or oily, and a gentle freshness and cleanliness. It also had good makeup retention, showed no change with respect to temperature or time, and was very stable.

Example 10

Manufacture of Cream

After dispersing particulate titanium oxide of mean particle diameter 0.05um in water to a concentration of 10%, adding 10% sodium silicate solution (SiO2/Na2O mol ratio: 0.5) corresponding to 2% relative to titanium oxide in terms of SiO2 conversion, and stirring well, 10% aluminium sulfate solution corresponding to 7.5% relative to titanium oxide in terms of Al2O3 conversion was added gradually, and silicic acid hydrate and alumina hydrate were deposited on the surface of the titanium oxide. After termination of the reaction, filtering, washing and drying, the product was pulverized by a jet mill. This was moved to a Henschel mixer, 1% of the silicone 1 obtained in Example 1 was added with sufficient stirring, and after mixing and stirring, the product was baked at 120° C. to give a hydrophobic-treated particulate titanium oxide powder.

Next, a cream was manufactured by processing the ingredients below according to the following process.

| Ingredient | Proportion (weight %) |
|---|---|
| 1. Dimethylpolysiloxane (6 cs) | 6.0 |
| 2. Methyl phenyl polysiloxane | 4.0 |
| 3. Squalane | 5.0 |
| 4. Neopentyl glycol dioctanate | 3.0 |
| 5. Polyether denatured silicone (Shin-Etsu Chemical Co., Ltd., KF6012) | 3.0 |
| 6. Above-mentioned hydrophobic particulate titanium oxide | 2.0 |
| 7. Magnesium sulfate | 0.7 |
| 8. Glycerol | 10.0 |
| 9. Antiseptics | Suitable amount |
| 10. Perfume | Suitable amount |
| 11. Purified water | Remainder |

Manufacturing Method

Step A: Components 1–8 are mixed, component 5 is added, and the product mixed uniformly.

Step B: Components 7–9 and 11 are dissolved by heating.

Step C: After gradually adding the mixture obtained in step B to the mixture obtained in step A and emulsifying it with stirring, the product was cooled, and component 11 was added to obtain the cream.

The cream obtained was fine, had a light spread without being sticky or oily, and exuded a gentle freshness and cleanliness. It also had extremely good makeup retention, showed no change with respect to temperature or time, and was very stable.

Example 11
Manufacture of Sunscreen Milky Lotion 99 parts of particulate titanium oxide which had previously been heat-treated by pressure reduction and drying, was introduced into a reaction vessel, and a solution comprising the silicone 2 (1 part) obtained in Example 2 diluted in toluene was gradually added with stirring. The temperature was then raised to distil off the toluene, and the product was baked with stirring for 3 hours at 150° C. The powder was returned to room temperature in a current of nitrogen, and used.

Next, a sunscreen milky lotion was manufactured by processing the ingredients below according to the following process.

| Ingredient | Proportion (weight %) |
| --- | --- |
| 1. Decamethyl cyclopentasiloxane | 20.0 |
| 2. Methylphenyl polysiloxane | 3.0 |
| 3. Monoisostearic acid sorbitan | 1.0 |
| 4. Polyether denatured silicone (Shin-Etsu Chemical Co., Ltd., KF6015) | 0.5 |
| 5. Trimethylsiloxy silicic acid | 1.0 |
| 6. Paramethoxy octyl cinnamate | 4.0 |
| 7. Particulate titanium oxide treated with silicone | 28.0 |
| 8. Sorbitol | 2.0 |
| 9. Sodium chloride | 2.0 |
| 10. Antiseptics | Suitable amount |
| 11. Perfume | Suitable amount |
| 12. Purified water | Remainder |

Manufacturing Method

Step A: Components 1–6 are mixed, component 7 is added, and the product mixed uniformly.

Step B: Components 8–10 and 12 are dissolved by heating.

Step C: After gradually adding the mixture obtained in step B to the mixture obtained in step A and emulsifying it with stirring, the product was cooled, and component 11 was added to obtain the sunscreen milky lotion.

The sunscreen milky lotion obtained was fine, had a light spread without being sticky or oily, and exuded a gentle freshness and cleanliness. As it also had good makeup retention, it provided long-lasting protection against ultraviolet radiation, showed no change with respect to temperature or time, and was very stable.

Example 12
Manufacture of Liquid Emulsion Foundation 99 parts each of particulate titanium oxide, mica titanium, titanium oxide, red ocher, and yellow iron oxide and black iron oxide powders which had previously been heat-treated by pressure reduction and drying, were respectively introduced into a reaction vessel, and a solution comprising the silicone 3 (1 part) obtained in Example 3 diluted in toluene was gradually added with stirring. The temperature was then raised to distil off the toluene, and the product was baked with stirring for 3 hours at 150° C. The powder was returned to room temperature in a current of nitrogen, and used.

Next, a liquid emulsion foundation was manufactured by processing the ingredients below according to the following process.

| Ingredient | Proportion (weight %) |
| --- | --- |
| 1. Decamethylcyclopentasiloxane | 16.0 |
| 2. Dimethylpolysiloxane (6 cs) | 8.0 |
| 3. Paramethoxy octyl cinnamate | 3.0 |
| 4. 12-hydroxy stearic acid | 1.0 |
| 5. Fluorine denatured silicone (Shin-Etsu Chemical Co., Ltd., FL-100) | 15.0 |
| 6. Polyether denatured silicone (polyoxyethylene trifluoropropyl denatured silicone) | 5.0 |
| 7. Spherical silicone resin powder (Shin-Etsu Chemical Co., Ltd., KMP590) | 3.0 |
| 8. Particulate titanium oxide treated with silicone 3 | 8.0 |
| 9. Titanium mica treated with silicone 3 | 1.0 |
| 10. Titanium oxide treated with silicone 3 | 5.0 |
| 11. Red ocher treated with silicone 3 | 0.9 |
| 12. Yellow iron oxide treated with silicone 3 | 2.0 |
| 13. Black iron oxide treated with silicone 3 | 1.0 |
| 14. Ethanol | 15.0 |
| 15. Glycerol | 3.0 |
| 16. Magnesium sulfate | 1.0 |
| 17. Antiseptics | Suitable amount |
| 18. Perfume | Suitable amount |
| 19. Purified water | Remainder |

Manufacturing Method

Step A: Components 7–13 are mixed, and the product mixed uniformly.

Step B: Components 1–6 are mixed with heating to 70° C., the mixture obtained in step A is added, and the product dispersed uniformly.

Step C: Components 14–17 and 19 are heated to 40° C., this was gradually added to the mixture obtained in step B to the mixture obtained in step A to emulsify it, then the product was cooled, and component 18 was added to obtain the liquid foundation.

The liquid foundation obtained had no stickiness, had a light spread, and exuded a clean coolness. It also showed no change with respect to temperature and time, and had excellent stability.

Example 13
Manufacture of Eyeliner 99 parts of black iron oxide powder which had previously been heat-treated by pressure reduction and drying was introduced into a reaction vessel, and a solution comprising the silicone 1 (1 part) obtained in Example 1 diluted in toluene was gradually added with stirring. The temperature was then raised to distil off the toluene, and the product was baked with stirring for 3 hours at 150° C. The powder was returned to room temperature in a current of nitrogen, and used.

Next, an eyeliner was manufactured by processing the ingredients below according to the following process.

| Ingredient | Proportion (weight %) |
| --- | --- |
| 1. Decamethylcyclopentasiloxane | 22.0 |
| 2. Dimethylpolysiloxane (6cs) | 5.0 |
| 3. Black iron oxide treated with silicone 1 | 20.0 |
| 4. Vitamin E cellulose acetate | 0.2 |
| 5. Jojoba oil | 2.0 |
| 6. Bentonite | 3.0 |

-continued

| Ingredient | Proportion (weight %) |
| --- | --- |
| 7. Polyether denatured silicone (Shin-Etsu Chemical Co., Ltd., KF6017) | 2.0 |
| 8. Ethanol | 10.0 |
| 9. 1, 3-butylene glycol | 10.0 |
| 10. Antiseptics | Suitable amount |
| 11. Perfume | Suitable amount |
| 12. Purified water | Remainder |

Manufacturing Method

Step A: Components 1, 2 are mixed, component 3 is added, and the product is uniformly dispersed.

Step B: Components 8–10 and 12 are mixed.

Step C: The mixture obtained in step B is added to the mixture obtained in step A, then the product is emulsified, cooled, and component 11 is added to obtain an eye liner.

The eyeliner obtained had a light spread, was easy to draw, and had a cool and clean feel without stickiness. It also had excellent water resistance and antiperspirant properties, and very good makeup retention.

Example 14
Manufacture of Cream 99 parts of particulate titanium oxide which had previously been heat-treated by pressure reduction and drying, was introduced into a reaction vessel, and a solution comprising the silicone 3 (1 part) obtained in Example 3 diluted in toluene was gradually added with stirring. The temperature was then raised to distil off the toluene, and the product was baked with stirring for 3 hours at 150° C. The powder was returned to room temperature in a current of nitrogen, and used.

Next, a cream was manufactured by processing the ingredients below according to the following process.

| Ingredient | Proportion (weight %) |
| --- | --- |
| 1. Decamethylcyclopentasiloxane | 16.0 |
| 2. Dimethylpolysiloxane (6cs) | 4.0 |
| 3. Polyether-denatured silicone (Shin-Etsu Chemical Co., Ltd., brand name KF6017) | 5.0 |
| 4. POE(5) octyldodecyl ether | 1.0 |
| 5. Monostearin acid polyoxyethylene sorbitan (20E.O.) | 0.5 |
| 6. Silicic acid anhydride-treated zinc oxide (silica of 0.01-10 μm particle diameter of which 50% contains zinc oxide, Asahi Glass Co., Ltd., brand name Sunsphere SZ-5) | 2.0 |
| 7. Particulate titanium oxide treated with silicone 3 | 10.0 |
| 8. Liquid paraffin | 2.0 |
| 9. Macadamia nut oil | 1.0 |
| 10. Ougon extract (extracted with 50% 1, 3-butylene glycol water) | 1.0 |
| 11. Gentiana extract (extracted with 20% ethanol water) | 0.5 |
| 12. Ethanol | 5.0 |
| 13. 1, 3-butylene glycol | 2.0 |
| 14. Antiseptics | Suitable amount |
| 15. Perfume | Suitable amount |
| 16. Purified water | Remainder |

Manufacturing Method

Step A: Components 6–9 are mixed and uniformly dispersed.

Step B: Components 1–5 are mixed, and the mixture obtained in step A is added.

Step C: Components 10–14 and 16 are mixed, the mixture obtained in step B is added, and the product emulsified.

Step D: The mixture obtained in Step C is cooled, and component 15 is added to obtain the cream.

The cream obtained had no stickiness, light spread, excellent adhesion, coolness and a glossy finish. It had excellent makeup retention, no change with respect to temperature or time, and excellent stability.

Example 15
Manufacture of Foundation

A foundation was manufactured by processing the ingredients below according to the following process.

| Ingredient | Proportion (weight %) |
| --- | --- |
| 1. Decamethylcyclopentasiloxane | 27.0 |
| 2. Methylphenyl polysiloxane | 3.0 |
| 3. Glyceryl triiso-octanate | 10.0 |
| 4. Polyether denatured silicone (Shin-Etsu Chemical Co., Ltd.,KF6026) | 1.0 |
| 5. Polyglyceryl monoisostearate | 3.0 |
| 6. Hydrophobic treated mixing powder (refer to following process A) | 18.0 |
| 7. Red ocher | 1.2 |
| 8. Yellow iron oxide | 2.6 |
| 9. Black iron oxide | 0.2 |
| 10. 1, 3-butylene glycol | 7.0 |
| 11. Sodium chloride | 0.5 |
| 12. Antiseptics | Suitable amount |
| 13. Perfume | Suitable amount |
| 14. Purified water | Remainder |

Manufacturing Method

Step A: 8.0 parts particulate titanium oxide, 4.0 parts particulate zinc oxide, 3.0 parts talc and 3.0 parts mica were mixed, 1 weight % of the silicone 2 obtained in Example 2 was added to these powders, and the mixture is heated to obtain a hydrophobic mixed powder (Component 6).

Step B: Components 1–5 are mixed and dissolved by heating, and Components 6–9 are uniformly dispersed in the product.

Step C: Components 10–12 and 14 are mixed, the mixture obtained in the step B is added, and the product emulsified.

Step D: The mixture obtained in Step C is cooled, and Component 13 is added to obtain the foundation.

The foundation obtained had no stickiness, light spread, excellent adhesion, coolness and a glossy finish. It had excellent makeup retention, no change with respect to temperature or time, and excellent stability.

Example 16
Manufacture of a Sun-Cut Cream 99 parts of particulate zinc oxide which had previously been heat-treated by pressure reduction and drying, was introduced into a reaction vessel, and a solution comprising the silicone 3 (1 part) obtained in Example 3 diluted in toluene was gradually added with stirring. The temperature was then raised to distil off the toluene, and the product was baked by stirring for 3 hours at 150° C. The powder was returned to room temperature in a current of nitrogen, and used.

Next, a sun-cut cream was manufactured by processing the ingredients below according to the following process.

| Ingredient | Proportion (weight %) |
|---|---|
| 1. Decamethylcyclopentasiloxane | 17.5 |
| 2. Acryl silicone (Shin-Etsu Chemical Co., Ltd., KP545) | 12.0 |
| 3. Glyceryl triiso-octanate | 5.0 |
| 4. Paramethoxy octyl cinnamate | 6.0 |
| 5. Silicone gel (Shin-Etsu Chemical Co., Ltd., KSG21) | 5.0 |
| 6. Polyether denatured silicone (polyoxyalkylene and alkyl denatured organopolysiloxane, Shin-Etsu Chemical Co., Ltd., KF6026) | 1.0 |
| 7. Silicone 3-treated zinc oxide | 20.0 |
| 8. Sodium chloride | 0.5 |
| 9. 1, 3-butylene glycol | 2.0 |
| 10. Antiseptics | Suitable amount |
| 11. Perfume | Suitable amount |
| 12. Purified water | Remainder |

Manufacturing Method

Step A: Component 2 is added to part of component 1, mixed uniformly, then component 7 is added, and dispersed by a bead mill.

Step B: The remainder of components 1 and 3–6 are mixed, and mixed uniformly.

Step C: Components 8–10 and 12 are mixed and dissolved.

Step D: The mixture obtained in Step C is added to the mixture obtained in Step B, the product emulsified, and the compound obtained in Step A added with component 11 to obtain the sun-cut cream.

The sun-cut cream obtained had no stickiness, light spread, excellent adhesion, coolness and a glossy finish. It had excellent makeup retention, and was very stable with respect to temperature and time.

Advantages of the Invention

The powder treated by the silicone compound of this invention has miscibility with ordinary oil, fluorinated oil and silicone oil, and the stability of the emulsion in these combined usage systems is improved. Further, the powder treated by the silicone compound has excellent water-repellent properties and good dispersibility in volatile oils such as octamethylcylotetrasiloxane and decamethylcyclopentasiloxane, and it is easy to use as a powder for makeup.

If the powder treated by this silicone compound is used for an emulsification system, it has an outstanding emulsification capacity without loss of affinity with oils generally used for makeup such as other silicone oils, ester oil and hydrocarbon oil, and as the stability of the emulsion with time is good, it has very wide application to cosmetics.

The makeup of this invention with which the powder surface-treated by the silicone compound of this invention has been blended, had a light spread without being oily, and felt fresh and clean. It also had excellent makeup retention, showed no change with respect to temperature or time and had excellent stability.

What is claimed is:

1. A silicone compound represented by the general formula (1):

$$R^1_a R^2_b R^3_c SiO_{(4-a-b-c)/2}$$

in the formula, $R^1$ is at least one organic group having 1–30 carbon atoms chosen from alkyl, aryl, aralkyl, fluorine-substituted alkyl or organopolysiloxanylsilyl, $R^2$ is a reactive substituent group chosen from hydrogen, hydroxy or alkoxy having 1–6 carbon atoms, or a reactive substituent group in which at least one of carbon, oxygen and silicon are bonded to these reactive substituent groups, $R^3$ is a carboxylate residue represented by the following general formula (2):

$$R^4CO_2—Q—$$

$R^4$ is a saturated or unsaturated hydrocarbon group having 2–30 carbon atoms, Q is a bivalent hydrocarbon group which may also contain a hetero atom, a is 1.0–2.5. b is 0.001–1.5, and c is 0.001–1.5.

2. A silicone compound as defined in claim 1, wherein $R^3$ is a carboxylate residue represented by the general formula (3):

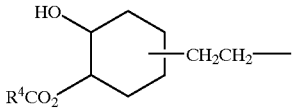

in the formula, $R^4$ is a saturated or unsaturated hydrocarbon group having 2–30 carbon atoms.

3. A silicone compound as defined in claim 1, wherein $R^4$ is a resin acid residue of a tricyclic diterpene carboxylic acid.

4. A silicone compound as defined in claim 1, wherein at least part of $R^1$ is represented by the following general formula (4):

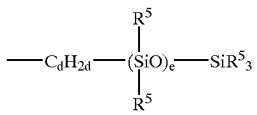

in the formula, R5 may respectively be identical or different, and is at least one substituent group chosen from alkyl having 1–30 carbon atoms, aryl, aralkyl, fluorine-substituted alkyl or hydroxyl, d is 1–5, and e is 0–500.

5. A powder surface-treated by a silicone compound as defined in claim 1, having a proportion of 0.1–30 weight parts relative to 100 weight parts of powder.

6. A makeup comprising 0.1–99.9 weight % of a) a silicone compound as defined in claim 5, and 0.1–99.9 weight % of b) a compound comprising alcoholic hydroxyl groups in the molecular structure.

7. A makeup as defined in claim 6, further comprising 90.0 weight parts of c) an oil.

8. A makeup as defined in claim 7, further comprising d) 99.0 weight parts of water.

9. A makeup as defined in claim 8, further comprising e) a powder other than said surface-treated powder, and/or a colouring agent.

10. A makeup as defined in claim 8, further comprising f) a surfactant.

11. A makeup as defined in claim 8, further comprising g) a cross-linked organopolysiloxane.

12. A makeup as defined in claim 8, further comprising h) a silicone resin.

13. A skin care product, at least part of which comprises a makeup as defined in claim 8.

14. A hairdressing product, at least part of which comprises a makeup as defined in claim 8.

15. An antiperspirant, at least part of which comprises a makeup as defined in claim 8.

16. A makeup product, at least part of which comprises a makeup as defined in claim 8.

17. An ultraviolet defense product, at least part of which comprises a makeup as defined in claim 8.

18. A makeup as defined in claim 8, which is a liquid, emulsion, cream, solid, paste, gel, powder, laminate, mousse or spray.

19. A makeup as defined in claim 13, which is a liquid, emulsion, cream, solid, paste, gel, powder, laminate, mousse or spray.

20. A makeup as defined in claim 14, which is a liquid, emulsion, cream, solid, paste, gel, powder, laminate, mousse or spray.

21. A makeup as defined in claim 15, which is a liquid, emulsion, cream, solid, paste, gel, powder, laminate, mousse or spray.

22. A makeup as defined in claim 16, which is a liquid, emulsion, cream, solid, paste, gel, powder, laminate, mousse or spray.

23. A makeup as defined in claim 17, which is a liquid, emulsion, cream, solid, paste, gel, powder, laminate, mousse or spray.

24. A method of synthesizing a silicone compound as defined in claim 1, comprising the synthesis of an alicyclic epoxy-modified silicone by an addition reaction of a main chain siloxane which is an organohydrogen polysiloxane to a vinyl alicyclic epoxide, and the reaction of a saturated or unsaturated carboxylic acid therewith.

25. A method of synthesizing a silicone compound as defined in claim 2, comprising the synthesis of an alicyclic epoxy-modified silicone by an addition reaction of a main chain siloxane which is an organohydrogen polysiloxane to a vinyl alicyclic epoxide, and the reaction of a saturated or unsaturated carboxylic acid therewith.

26. A method of synthesizing a silicone compound as defined in claim 3, comprising the synthesis of an alicyclic epoxy-modified silicone by an addition reaction of a main chain siloxane which is an organohydrogen polysiloxane to a vinyl alicyclic epoxide, and the reaction of a saturated or unsaturated carboxylic acid therewith.

27. A method of synthesizing a silicone compound as defined in claim 4, comprising the synthesis of an alicyclic epoxy-modified silicone by an addition reaction of a main chain siloxane which is an organohydrogen polysiloxane to a vinyl alicyclic epoxide, and the reaction of a saturated or unsaturated carboxylic acid therewith.

* * * * *